(12) United States Patent
Tomaka et al.

(10) Patent No.: US 6,651,844 B2
(45) Date of Patent: Nov. 25, 2003

(54) SPRAY DISPENSER COUNTER

(75) Inventors: Jeffrey S. Tomaka, New York, NY (US); Jason S. Spitz, Whitehouse Station, NJ (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 10/081,939

(22) Filed: Feb. 22, 2002

(65) Prior Publication Data

US 2003/0160061 A1 Aug. 28, 2003

(51) Int. Cl.$^7$ .................................................. B67D 5/22
(52) U.S. Cl. ........................ 222/38; 222/39; 222/644; 222/321.6
(58) Field of Search ........................ 222/32, 36, 38, 222/39, 30, 641, 644, 646, 321.6, 321.9, 402.2; 128/200.14, 205.23

(56) References Cited

U.S. PATENT DOCUMENTS

| | | | |
|---|---|---|---|
| 4,034,757 A | 7/1977 | Glover | 128/260 |
| 4,565,302 A | 1/1986 | Pfeiffer et al. | 222/38 |
| 4,817,822 A | 4/1989 | Rand et al. | 222/38 |
| 5,020,527 A | 6/1991 | Dessertine | 128/200.23 |
| 5,174,473 A | 12/1992 | Marelli | 222/38 |
| 5,209,375 A | 5/1993 | Fuchs | 222/38 |
| 5,300,042 A | 4/1994 | Kossoff et al. | 604/210 |
| 5,363,842 A | 11/1994 | Mishelevich et al. | 128/200.14 |
| 5,411,173 A | 5/1995 | Weinstein | 222/38 |
| 5,421,482 A | 6/1995 | Garby et al. | 222/36 |
| 5,482,030 A | 1/1996 | Klein | 128/200.23 |
| 5,497,764 A | 3/1996 | Ritson et al. | 128/200.14 |
| 5,505,192 A | 4/1996 | Samiotes et al. | 128/200.14 |
| 5,520,166 A | 5/1996 | Ritson et al. | 128/200.14 |
| 5,544,647 A | 8/1996 | Jewett et al. | 128/200.23 |
| 5,558,085 A | 9/1996 | Rubsamen et al. | 128/200.14 |
| 5,564,414 A | 10/1996 | Walker et al. | 128/200.23 |
| 5,622,163 A | 4/1997 | Jewett et al. | 128/200.23 |
| 5,676,129 A | 10/1997 | Rocci, Jr. et al. | 128/200.23 |
| 5,794,612 A | 8/1998 | Wachter et al. | 128/200.23 |
| 5,809,997 A | 9/1998 | Wolf | 128/200.23 |
| 5,819,726 A | 10/1998 | Rubsamen et al. | 128/200.14 |
| 5,871,007 A | 2/1999 | Clark, Jr. | 128/200.23 |
| 5,904,139 A | 5/1999 | Hauser | 128/200.23 |
| 6,029,659 A | 2/2000 | O'Connor | 128/203.12 |
| 6,138,669 A | 10/2000 | Rocci, Jr. et al. | 128/200.23 |
| 6,142,339 A | 11/2000 | Blacker et al. | 222/23 |
| 6,148,815 A | 11/2000 | Wolf | 128/205.23 |
| 6,155,251 A | 12/2000 | Hauser | 128/200.23 |
| 6,161,724 A | 12/2000 | Blacker et al. | 222/23 |
| 6,164,494 A | 12/2000 | Marelli | 222/38 |
| 6,202,642 B1 | 3/2001 | McKinnon et al. | 128/200.23 |
| 6,349,851 B1 * | 2/2002 | Lu | 222/39 |

FOREIGN PATENT DOCUMENTS

| | | |
|---|---|---|
| WO | WO 93/00951 | 1/1993 |
| WO | WO 95/26769 | 10/1995 |
| WO | WO 99/49920 | 10/1999 |
| WO | WO 01/28887 | 4/2001 |
| WO | WO 01/41845 | 6/2001 |
| WO | WO 01/41847 | 6/2001 |

* cited by examiner

*Primary Examiner*—Gene Mancene
*Assistant Examiner*—Patrick M Buechner
(74) *Attorney, Agent, or Firm*—Robert A. Franks (57) ABSTRACT

A counter for counting delivered doses from a spray dispenser of a type having a main body holding a fluid substance to be dispensed and a cap with a pump and nozzle mounted on the main body, the counter including: a counter body having an upper recess for receiving the main body; a button in an arcuate lower depression on the counter body for actuation by a person's thumb when a dose is dispensed; a display on the counter body for displaying a number of doses dispensed from the main body; a circuit which changes the number of doses display each time that the button is depressed; a set button for setting a starting number which is displayed on the display, corresponding to a predetermined number of doses remaining in the spray dispenser; and a sound generator which generates an audible sound upon each depression of the button.

9 Claims, 11 Drawing Sheets

SPRAY DISPENSER COUNTER

INTRODUCTION TO THE INVENTION

The present invention relates generally to spray dispensers and, more particularly, is directed to a counter for automatically counting the number of doses of sprays, such as nasal sprays, that have been dispensed by, or remain to be dispensed from, a hand-held fluid pump spray dispenser.

A typical known nasal spray pump dispenser includes a container that holds a fluid substance to be dispensed, along with a cap that is attached to the container, such as by screw threads or crimping. The cap includes a tapered atomizing nozzle and a pump that withdraws liquid from the interior of the main body by means of a suction dip tube and delivers an atomized spray through the nozzle.

Specifically, the pump includes a pump chamber that holds liquid withdrawn from the interior of the main body through the dip tube. A piston connects with the pump chamber, and is spring biased upwardly.

The nozzle is connected with a pusher or trigger in the form of opposing outwardly directed wings, a flange or an enlarged annular shoulder for actuating the pump. When the wings, flange or enlarged annular shoulder is pressed down against the spring force, a pressure is built up, which forces the liquid out through the small opening in the upper end of the nozzle, thereby atomizing the same. When the flange, wings or enlarged annular shoulder is released, the spring forces the nozzle back up, creating a vacuum in the dip tube that draws in additional fluid to be dispensed.

Fluid spray dispensers of this type are well known in the art. Examples of such similar dispensers are shown, for example, in U.S. Pat. Nos. 4,274,560; 4,944,429; and 5,433,343; the entire disclosures of which are incorporated herein by reference. Another example of a spray dispenser of this type is sold by Schering Corporation of Kenilworth, N.J. in connection with its mometasone furoate monohydrate suspension nasal spray, under the trademark "NASONEX." The NASONEX spray dispenser is shown in U.S. Design Pat. No. 355,844 which is incorporated herein by reference.

In the above type of spray dispenser, the metering pump is actuated by a reciprocating movement along an axis coincident with the nozzle dispensing axis, in order to pump metered portions of fluid from the container through the nozzle. Thus, the forces applied by the user are along the axis of pumping and dispensing. Specifically, a user grasps the dispenser between the thumb and the two fingers by placing the thumb at the bottom of the container and the index and middle fingers on top of the flange, wings or enlarged annular shoulder. By squeezing the index and middle fingers toward the thumb, the pump is actuated to dispense the spray.

There is, however, no indication as to how much of the fluid substance in the container has been dispensed, so a person has no practical way of accurately determining when to re-supply. Some spray containers are not able to reliably dispense their normal amounts for each actuation as the container contents become nearly depleted, since the dip tube is not able to withdraw the entire fill volume; it is therefore advisable to discontinue use of a container while a small amount of material remains inside, after the labeled number of sprays have been delivered. A further problem is that a person often neglects to use nasal spray products on a regular basis as directed, and therefore the pharmacological effect is reduced.

SUMMARY OF THE INVENTION

In accordance with an aspect of the present invention, a counter is provided for counting actuations of a pump spray dispenser of a type including a container main body for holding a fluid substance to be dispensed and a cap, having a pump and spray nozzle, mounted on the container main body. The counter includes a counter body having an upper recess for receiving a lower portion of the container main body therein; a button provided externally on a lower end of the counter body for engagement by a user and simultaneous activation by a user when the nozzle is slidably moved with respect to the container main body to actuate the pump and deliver a dose; a display on the counter body for displaying a number of doses remaining in or dispensed from the container main body; and an electronic circuit which decrements or increments the number of doses displayed by the display each time that the button is depressed.

The button is positioned at an underside of the counter body, and specifically, the counter body has an arcuate depression and the button is positioned in the arcuate depression for actuation by a thumb of a person when a dose is dispensed from the spray dispenser.

At least one set button is provided for setting an initial number which is displayed on the display, corresponding to a predetermined number of doses to be dispensed from, or remaining in, the spray dispenser.

An optional sound generator generates an audible sound upon each depression of the button. The circuit includes a central processing unit which decrements or increments the number of doses displayed by the display each time that the button is depressed and, in response to a signal from the at least one set button, sets a starting number which is displayed on the display, corresponding to a predetermined number of doses dispensed from or remaining in the spray dispenser. The central processing unit also actuates the sound generator to generate the audible sound upon each depression of the button.

The central processing unit also controls the sound generator to generate an audible sound a predetermined time interval after the button has been depressed if the button has not been depressed again during the predetermined time interval.

The above and other features of the invention will become readily apparent from the following detailed description thereof, which is to be read in connection with the accompanying drawings.

DETAILED DESCRIPTION

Referring to the drawings in detail, a nasal spray device 10 with which the present invention can be used includes a container main body 12 that holds a fluid substance to be dispensed, along with a cap 14 that is removably or permanently mounted on the container. Although main body 12 is shown having a generally oval cross-sectional configuration, main body 12 can have any other suitable configuration, such as circular, square, triangular, rectangular, etc.

Cap 14 has a tapered atomizing nozzle 16 with an opening 16a at the upper end, and is attached to an atomizing pump (not shown) that withdraws liquid from the interior of main body 12 by means of a suction dip tube (not shown) and delivers an atomized spray through nozzle 16.

Specifically, the atomizing pump includes a pump chamber that holds liquid withdrawn from the interior of main body 12. An internal piston connects with the pump chamber, and is spring biased upwardly.

Nozzle 16 terminates at its lower end with an enlarged portion 18 of cap 14 that slidably fits on main body 12 and which includes an enlarged upper shoulder 20 at its upper end for actuating the pump. When upper shoulder 20 is pressed downward, by means of finger pressure on upper shoulder 20, pump pressure is built up which forces the fluid out through the small opening 16a in the upper end of nozzle 16, thereby atomizing the same. When enlarged upper shoulder 20 is released, the pump spring forces nozzle 16 upward, creating a vacuum that draws additional fluid through the dip tube into the pump chamber for dispensing.

Figure 3:
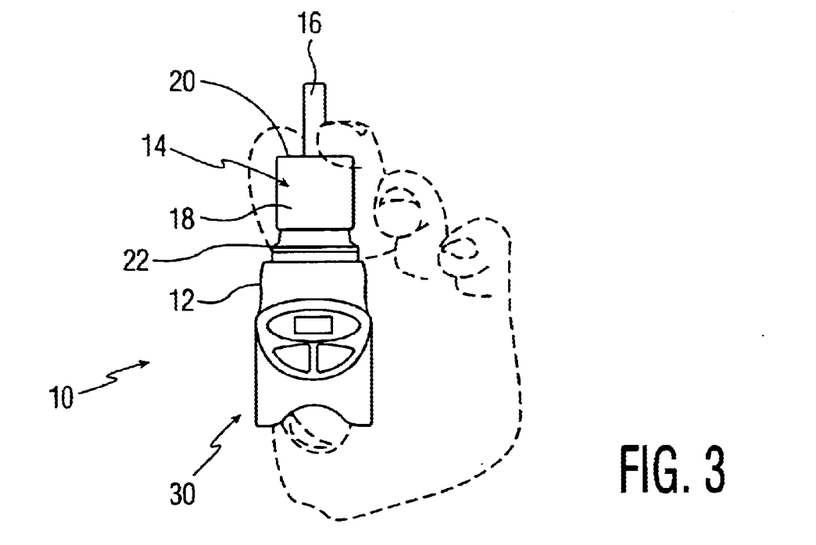
FIG. 3 is a perspective view of the nasal spray dispenser and counter of FIG. 1, with the cover removed, and being in an operative position in the hand of a person, shown in outline.
Figure 4:
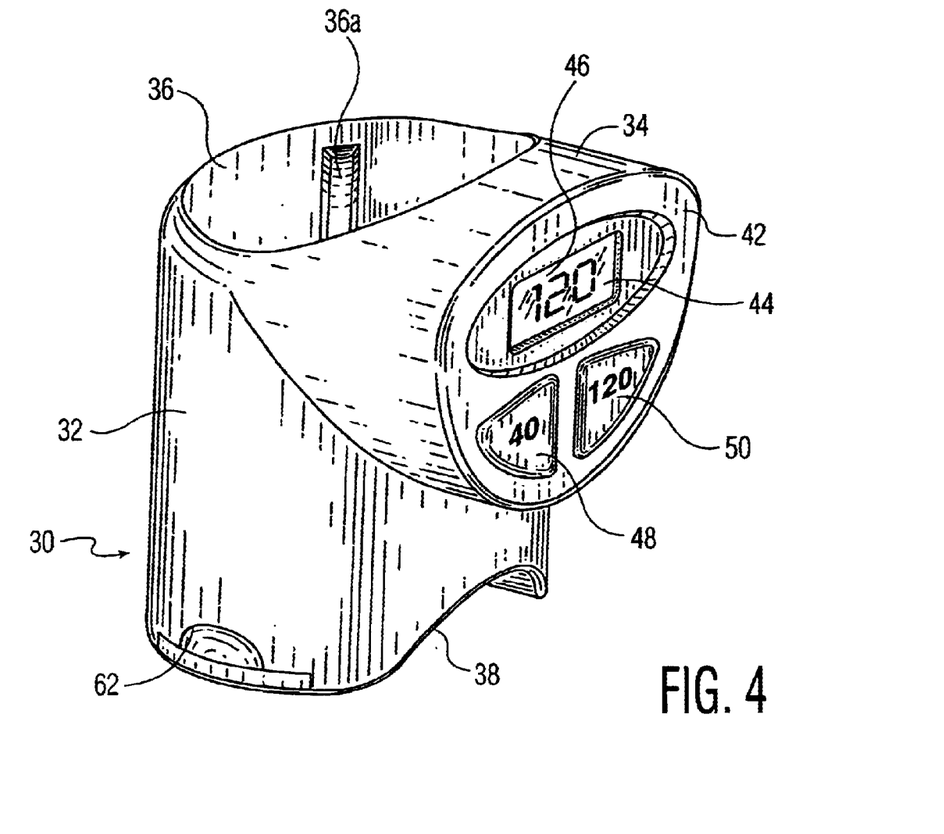
FIG. 4 is a perspective view of the counter according to the present invention.
Figure 5:
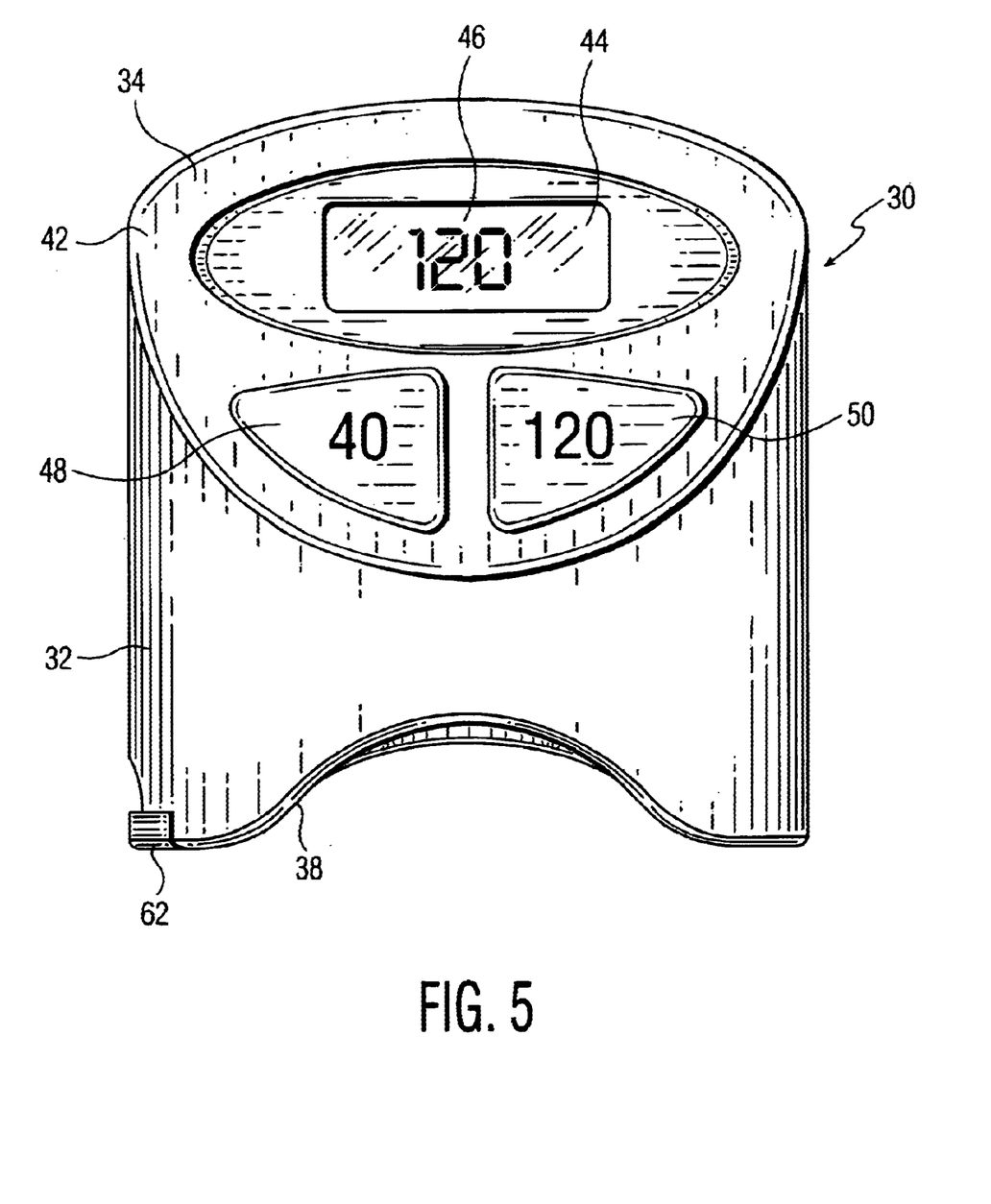
FIG. 5 is a front elevational view of the counter.
Figure 6:
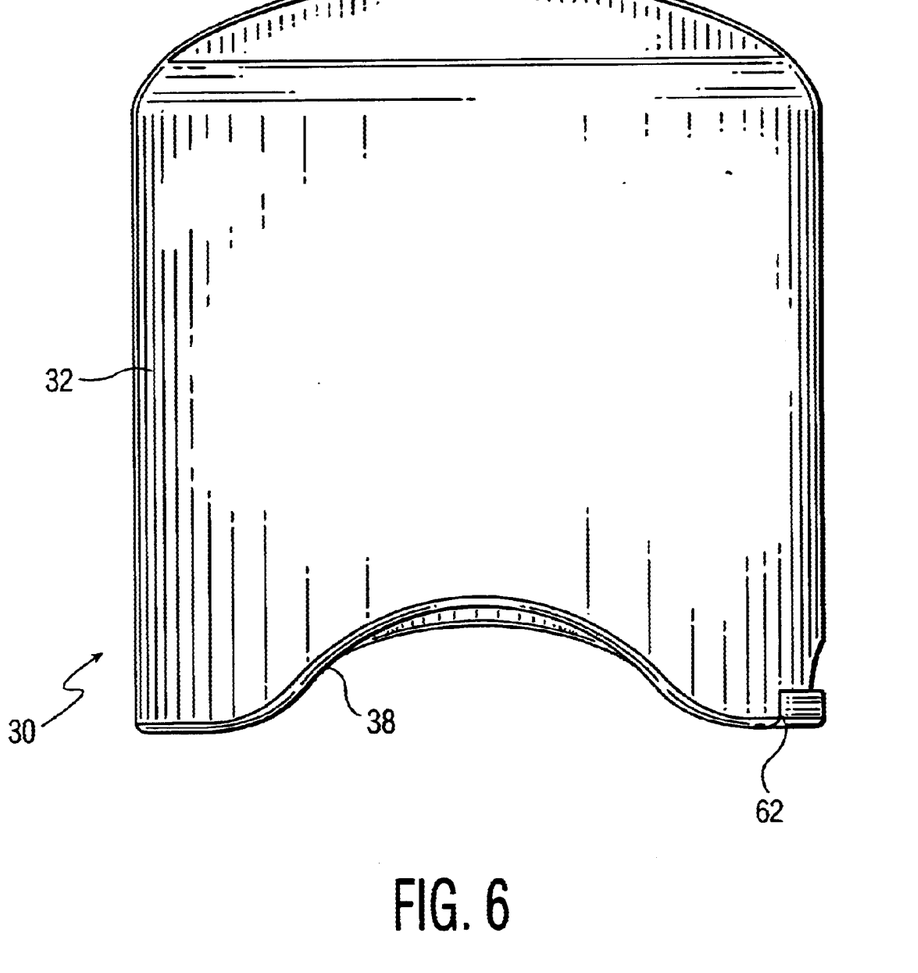
FIG. 6 is a rear elevational view of the counter.
Figure 7:
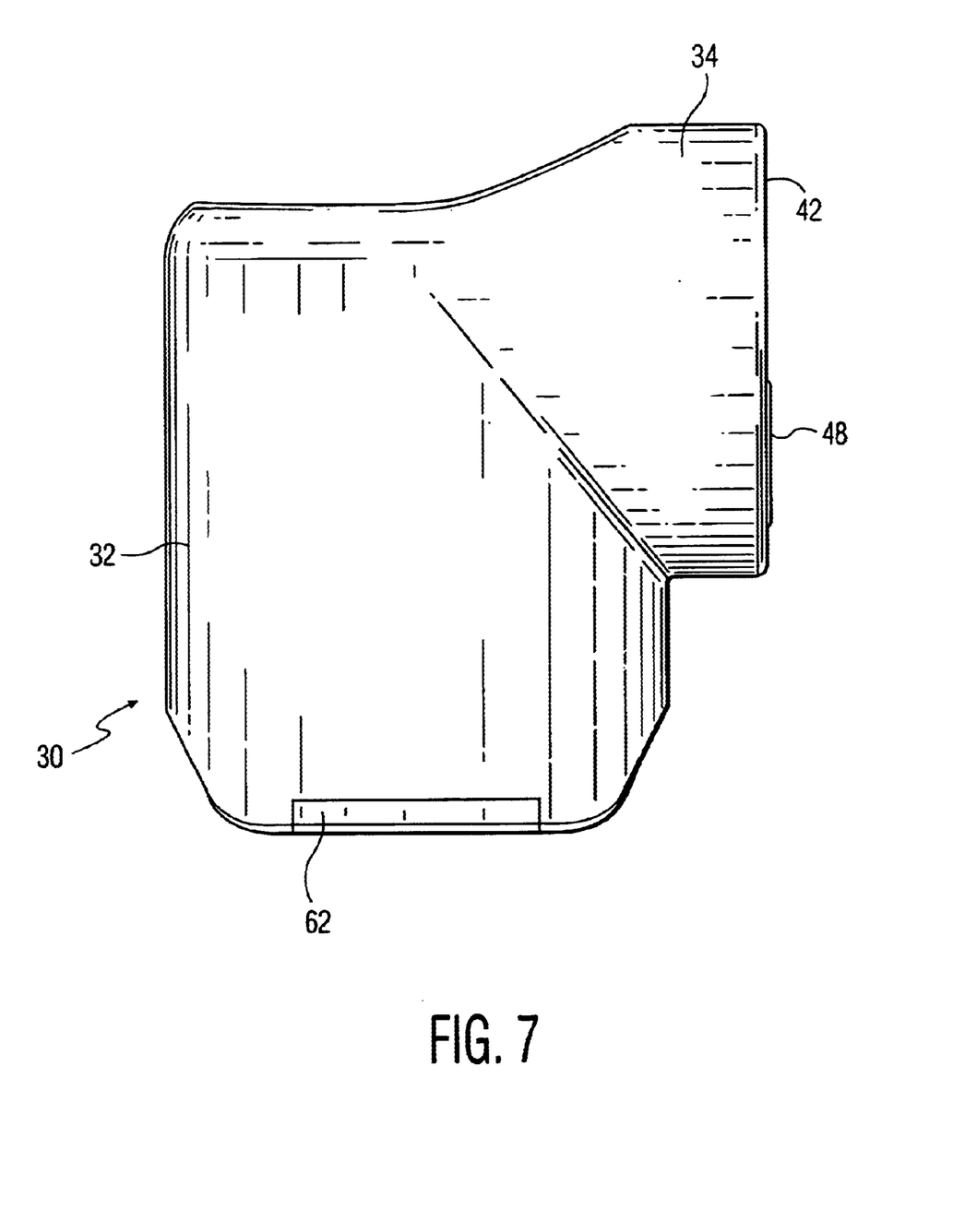
FIG. 7 is a side elevational view of the counter, the opposite side being a mirror image.
Figure 8:
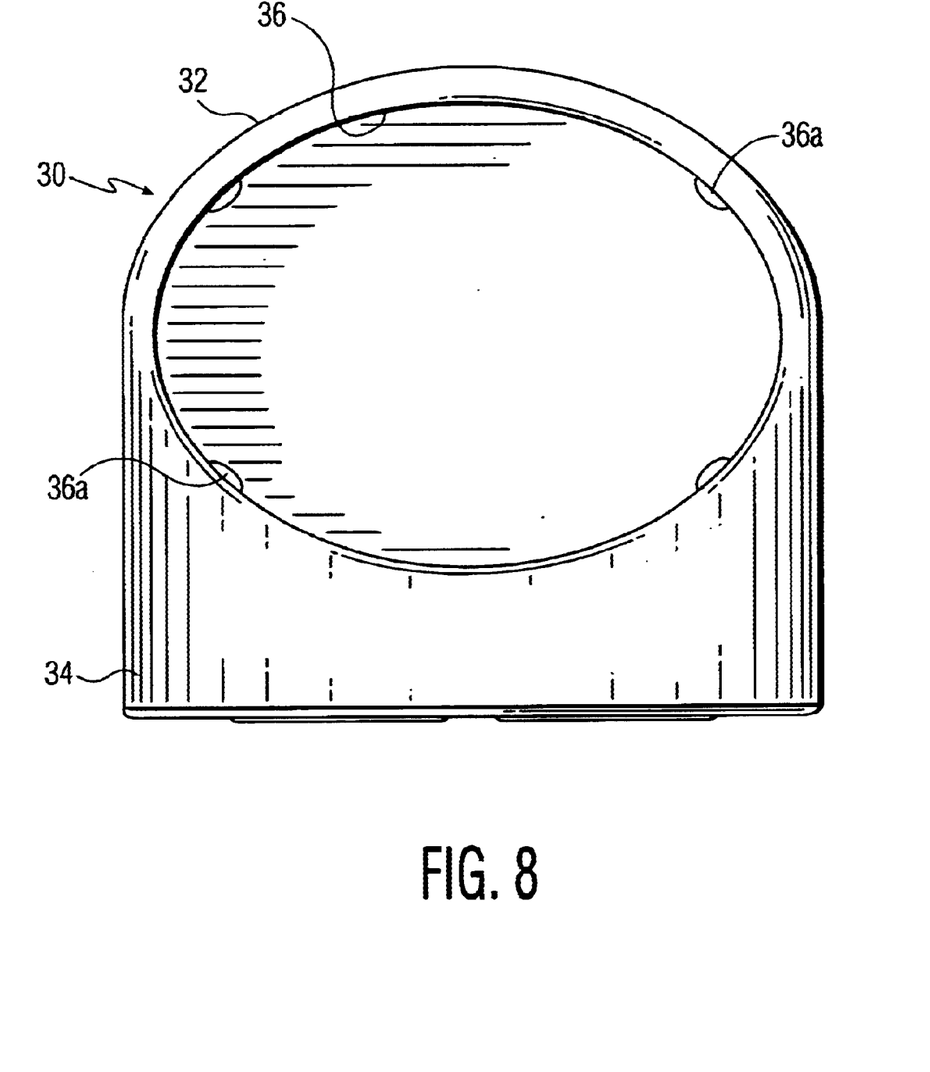
FIG. 8 is a top plan view of the counter.
Figure 9:
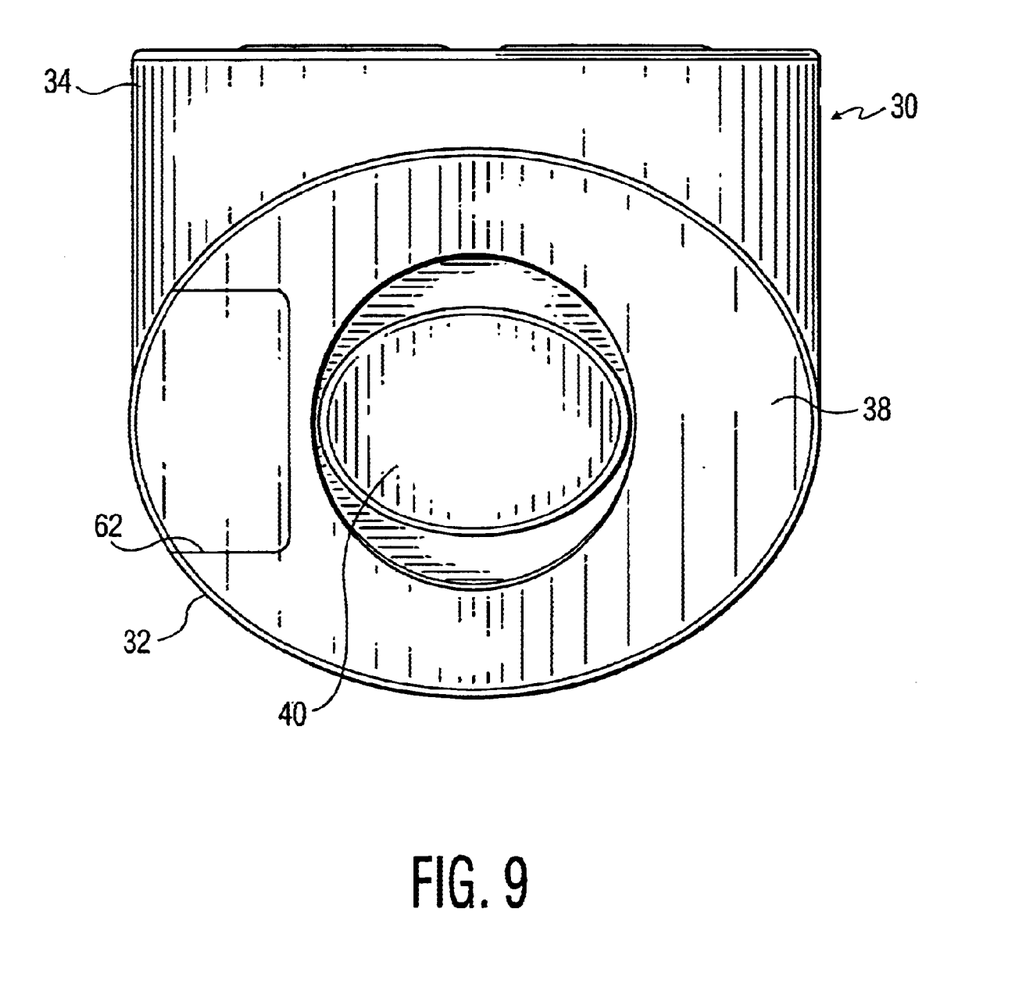
FIG. 9 is a bottom plan view of the counter.

In the above type of spray dispenser, the metering pump reciprocates along an axis coincident with the nozzle dispensing axis, in order to pump metered portions of fluid from container main body 12 through nozzle 16. Thus, the forces applied by the user are along the axis of pumping and dispensing. Specifically, the user grasps the dispenser between the thumb and the two fingers by placing his thumb at the bottom of container main body 12 and the index and middle fingers on top of enlarged upper shoulder 20, as shown in FIG. 3. By moving the index and middle fingers toward the thumb, the pump is actuated to dispense a spray.

Figure 1:
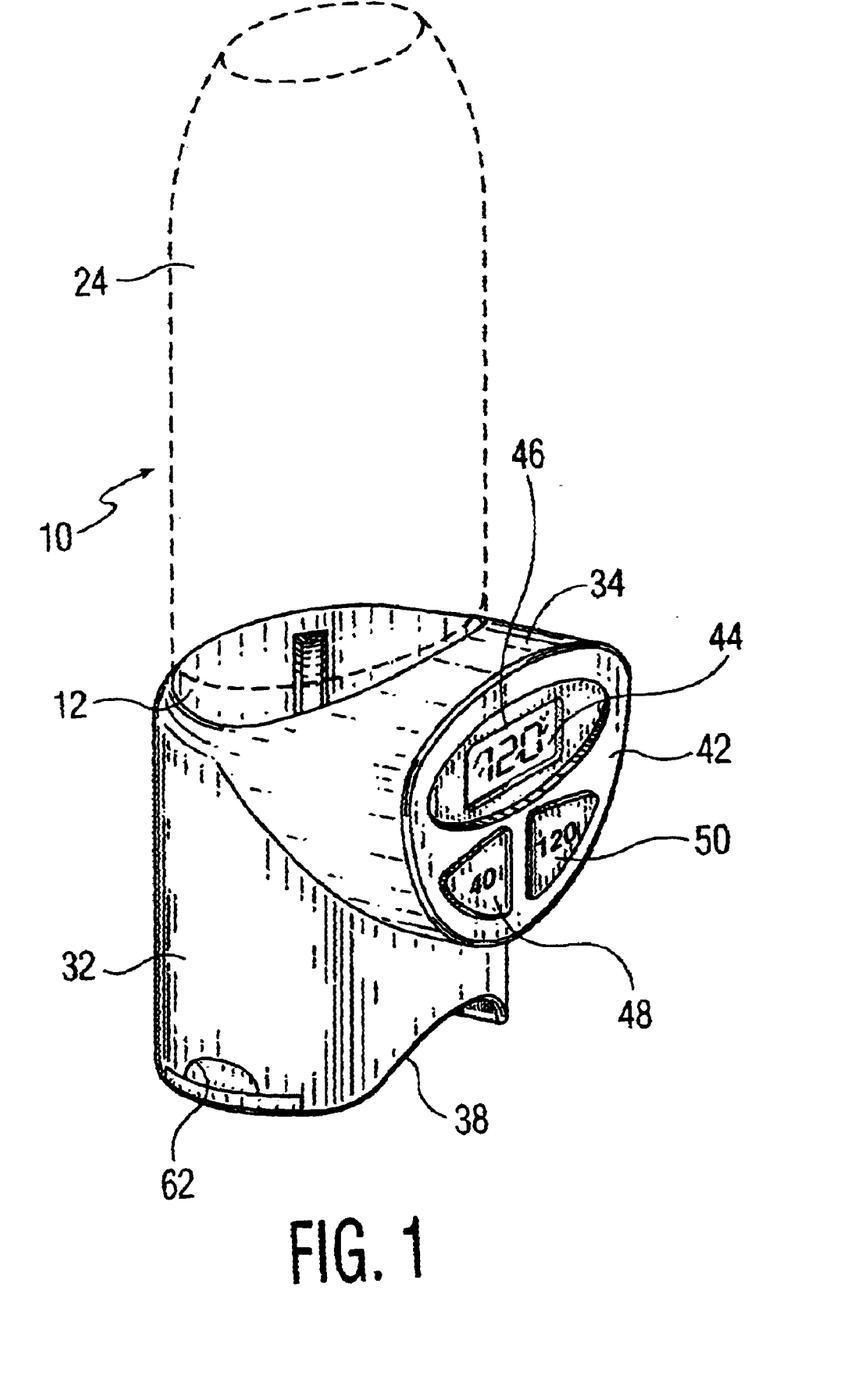
FIG. 1 is a perspective view of a nasal spray dispenser having a cover thereon, shown in outline, mounted to a counter device according to the present invention.
Figure 2:
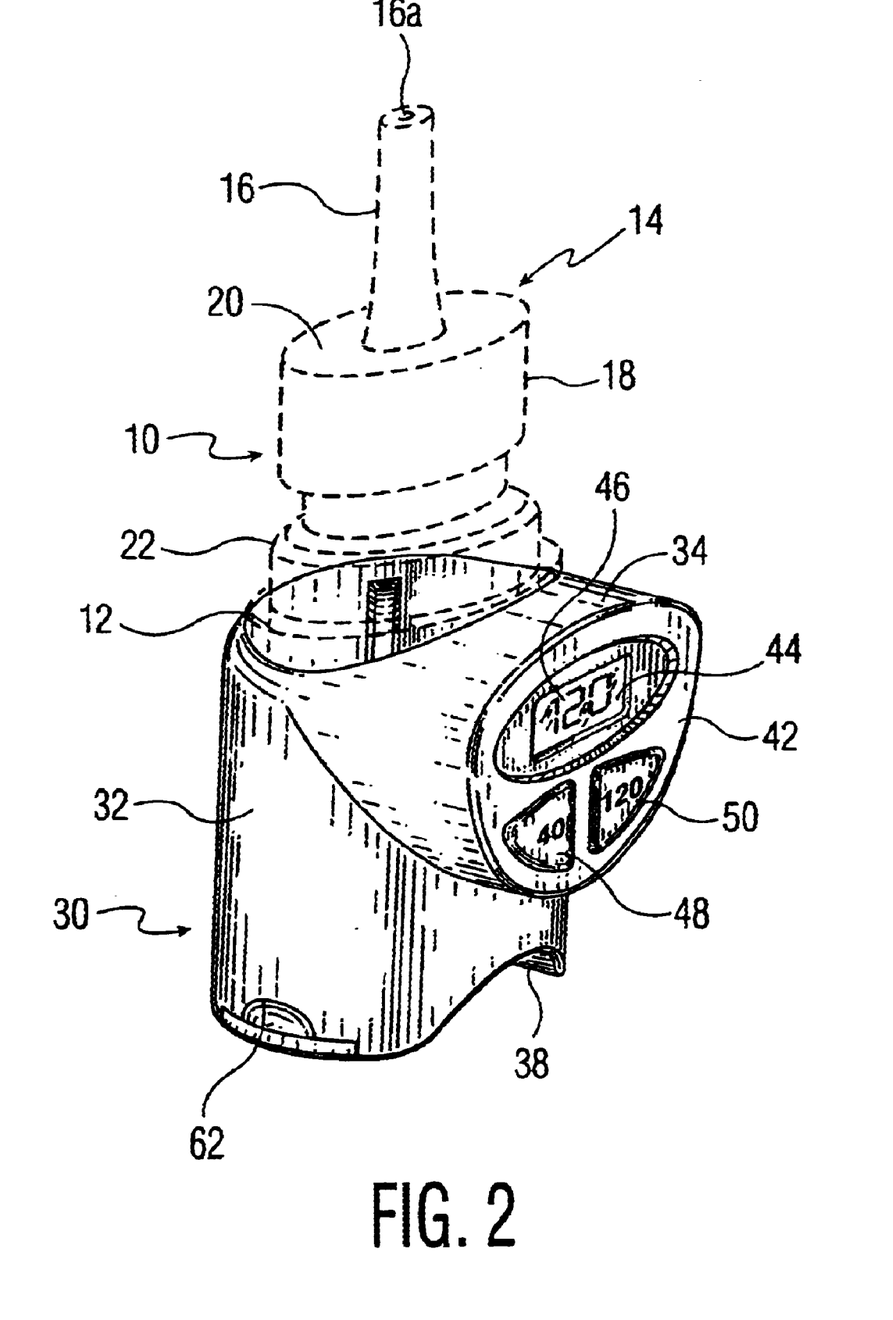
FIG. 2 is a perspective view of the nasal spray dispenser without a cover, shown in outline, mounted to a counter device according to the present invention.

Container main body 12 also includes an annular lip 22 immediately below the lower edge of enlarged portion 18. When nasal spray device 10 is not in use, a cover 24 can be positioned over nozzle 16 and enlarged portion 18. The inner dimensions of the lower end of cover 24 are such that cover 24 can have a releasable snap or friction fit over annular lip 22 in a known manner.

A more detailed explanation of nasal spray device 10 is not being provided since this element does not form part of the present invention and is well known in the art.

In accordance with the present invention, an electronic counter 30 is provided for use with nasal spray device 10. Specifically, counter 30 includes a main counter body 32 having a shape that typically, but not necessarily, approximates the exterior shape of the spray container with which it is to be used, with an extension body 34 extending transversely out from the upper portion of main counter body 30. The counter body cross-sectional shape is generally oval in the present drawings but the choice of any particular shape is not critical to the present invention and, as discussed, can be changed to approximate the shape of the spray device which is to be inserted.

A recess 36 having a generally oval cross-sectional configuration is provided in the upper end of main counter body 32 for receiving the lower end of container main body 12. In this regard, the dimensions and shape of recess 36 are such as to snugly but releasably hold container main body 12 therein. Ribs 36a can be optionally provided to assist with snugly holding container main body 12, these can be spaced at desired intervals and in desired numbers about recess 36 to form a friction fit with the outer wall of the container.

As an alternative to using the ribs, or to carefully controlling the dimensions and shape of the opening, the opening can be lined with a material having resilience or a tacky exterior surface, or both, which liner adapts to the size and shape of a spray container and snugly holds the container within the counter device. It is desired to hold the spray container to prevent its inadvertent separation from the counter, but to permit replacement of a spent spray container without undue effort.

The lower end of main counter body 32 has an arcuate depression 38, and a thumb button 40, either attached to or an integral part of an electrical switch, is provided centrally therein; the purpose of the thumb button will be understood more fully from the description hereinafter.

Extension body 34 has a front face 42 with a display 44. Any suitable display 44 can be used, for example, a 7-segment liquid crystal display (LCD), a light emitting diode (LED) display, or the like. Display 44 displays a number 46 indicating the number of doses remaining in nasal spray device 10 and counting downwardly to zero. Alternatively, display 44 can display the number of doses that have been used, thereby counting upwardly from zero. Although the invention is not limited to this embodiment, front face 42 includes two set buttons 48 and 50, one button indicating a first number of predetermined doses and the other button indicating a second number of predetermined doses. For example, the aforementioned pharmaceutical sold by Schering Corp. under the trademark "NASONEX" is currently made available in spray bottles having either 40 or 120 doses. For use with this product, button 48 would have the number "40" imprinted thereon and button 50 would have the number "120" imprinted thereon. Thus, for example, when a new nasal spray device 10 containing forty doses is installed, button 48 is held down for a predetermined amount of time, for example, five seconds, until a number 46 equal to "40" appears on display 44. Thereafter, every time that thumb button 40 is depressed upon delivery of a dose to the person, number 46 decrements by one.

The set buttons 48 and 50 are each either attached to or are integral parts of electrical switches, as will be readily appreciated by those skilled in the art.

Alternatively, rather than having a set button 48 or 50, one of the buttons can be used to progressively increment to a desired value, and the other button can be used to set that value as the initial value. Thus, there are various alternative arrangements that can be provided to adapt the counter for use with different products.

In the event that the counter is to be used in connection with a spray product that is available to dispense only one number of spray doses, a single set button will be sufficient.

Figure 10:
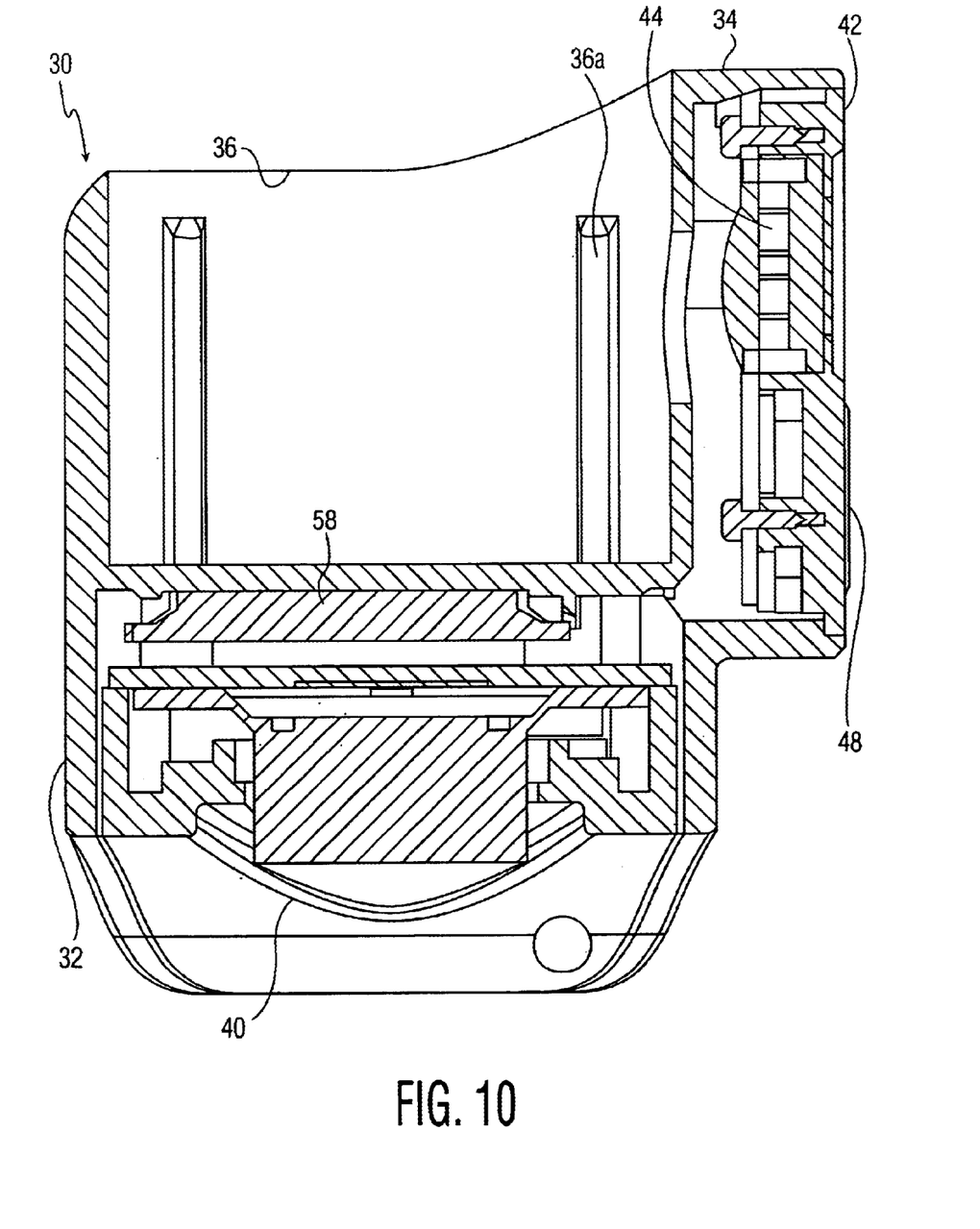
FIG. 10 is a cross-sectional view of the counter.
Figure 11:
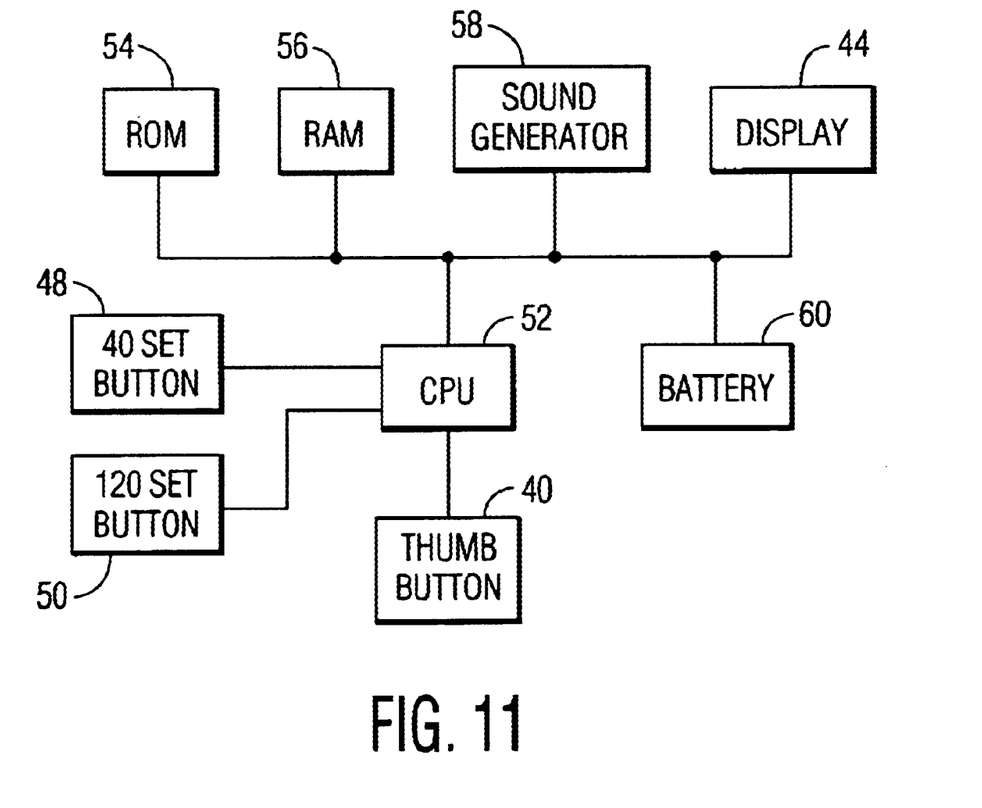
FIG. 11 is a block diagram of the electronic circuitry of the counter.

Referring now to FIGS. 10 and 11, the circuitry for counter 30 includes a central processing unit (CPU) 52 connected with set buttons 48 and 50 so that, upon actuation of either set button for the predetermined time, CPU 52 controls display 44 to display a number 46 corresponding to the number associated with the set button 48 or 50, for example, "40" or "120". In this regard, CPU 52 is connected with a read only memory (ROM) 54 for controlling the operating system using software programs, etc. for CPU 52, and is also connected with a non-volatile random access memory (RAM) or working memory 56 for storing the number 46 displayed on display 44.

Further, CPU 52 is connected with thumb button 40. Each time that thumb button 40 is depressed, CPU 52 receives a signal and actuates a sound generator 58 to emit an audible sound so that the person knows that thumb button 40 has been properly depressed. In this regard, sound generator 58 can be a beeper, buzzer or the like. At the same time, each depression of thumb button 40 causes CPU 52 to decrement the number 46 displayed on display 44 so that the person can know the number of doses remaining in the container.

In addition, CPU 52, based on the software stored in ROM 54, can optionally provide a time counting function. Specifically, in those circumstances where a person is supposed to take the medication on a daily basis, CPU 52 counts down twenty-four hours from each actuation of thumb button 40, and if thumb button 40 is not actuated again during that twenty-four hour period, CPU 52 controls sound generator 58 to generate an alarm sound to notify the person to again take the medication.

There is also a battery 60 in a compartment 62 in counter body 32 and which is connected to display 44, CPU 52, ROM 54, RAM 54 and sound generator 58 for supplying power to operate the same.

In operation, with container main body 12 positioned in recess 36, the user sets the number 46 on display 44 by depressing either set button 48 or 50 for a programmed predetermined time. Then, the user grasps the dispenser between the thumb and two fingers by placing the thumb on thumb button 40 at the bottom of the counter body 32 and the index and middle fingers on top of enlarged upper shoulder 20. By moving the index and middle fingers toward the thumb, the pump is actuated to dispense the spray. During pump actuation thumb button 40 is depressed, whereupon CPU 52 controls sound generator 58 to generate an audible sound and also decrements the number 46 displayed on display 44. This continues for each actuation until the number 46 displayed on display is zero, at which time the user knows to replace nasal spray device 10.

Although the present invention has been discussed in relation to a nasal spray device, it will be appreciated that any other type of spray dispenser can be used herewith. Fluids which can be delivered by spray devices include suspensions, emulsions and solutions, and can be intended for any number of different purposes including, without limitation thereto, therapeutic, cosmetic and hygienic purposes. Therapeutic nasal sprays are, however, an important use for the counter of this invention.

As a further modification, arcuate depression 38 can be eliminated or at least modified to have less of a curvature so that button 40 could be actuated by pressing it against the palm of a user's hand or other surface. However, it is typically desired to provide a small recess for the button, so that the button will not be depressed by merely placing the counter device on a flat surface between uses.

Figure 12:
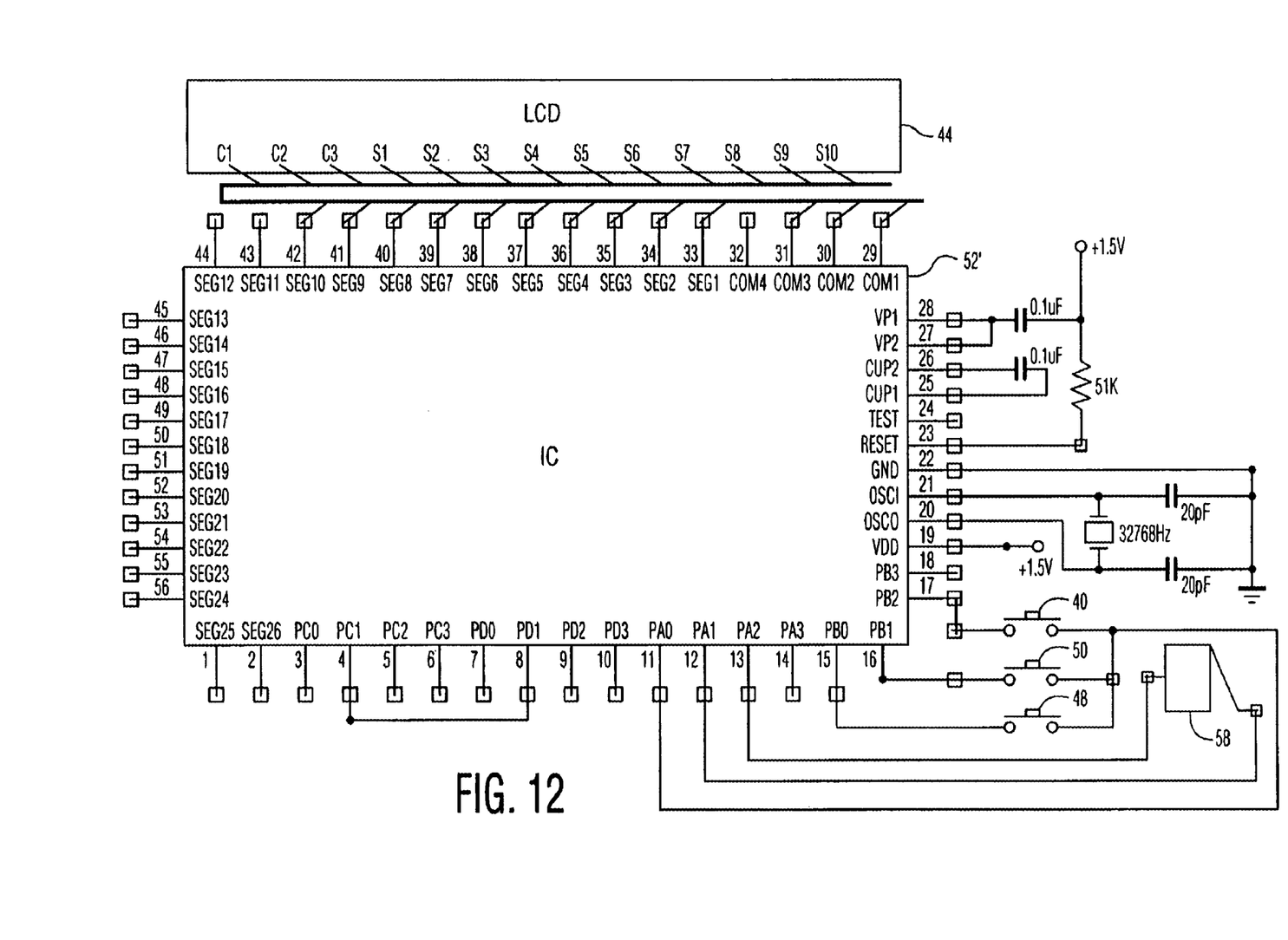
FIG. 12 is a diagram of modified electronic circuitry of the counter.

Further, rather than using CPU 52, a dedicated integrated circuit 52' specifically constructed for the present invention can be used in place thereof, for example as shown in the circuit diagram of FIG. 12.

Having described specific preferred embodiments of the invention with reference to the accompanying drawings, it will be appreciated that the present invention is not limited to those precise embodiments and that various changes and modifications can be effected therein by one of ordinary skill in the art without departing from the scope or spirit of the invention as defined by the appended claims.

What is claimed is:

1. A counter for counting delivered doses of a spray dispenser of a type having a container main body for holding a fluid substance to be dispensed and an attached cap having a spray actuator slidably mounted thereon, the counter comprising:
   a counter body having an upper recess for receiving a lower portion of the container main body therein;
   a button provided externally on a lower end of the counter body for engagement by a user and simultaneous activation by a user when the actuator is slidably moved with respect to the container main body to deliver a spray dose;
   a display on the counter body for displaying a number of doses remaining in or dispensed from said container main body; and
   a circuit which decrements or increments the number of doses displayed by the display each time that the button is depressed.

2. The counter according to claim 1, wherein said button is positioned at an underside of said counter body.

3. The counter according to claim 2, wherein said underside of said counter body has an arcuate depression and said button is positioned in said arcuate depression for actuation by a thumb of a person when a dose is dispensed from said spray dispenser.

4. The counter according to claim 1, further comprising at least one set button for setting a starting number which is displayed on said display, corresponding to a predetermined number of doses dispensed from or remaining in said spray dispenser.

5. The counter according to claim 1, further including a sound generator which generates an audible sound upon each depression of said button.

6. The counter according to claim 1, wherein said circuit includes a central processing unit which decrements or increments the number of doses displayed by the display each time that the button is depressed.

7. The counter according to claim 6, further comprising at least one set button for providing a signal to said central processing unit which, in response thereto, sets a number which is displayed on said display, corresponding to a predetermined number of doses dispensed from or remaining in said spray dispenser.

8. The counter according to claim 6, further including a sound generator which generates an audible sound, and wherein said central processing unit actuates said sound generator to generate said audible sound upon each depression of said button.

9. The counter according to claim 8, wherein said central processing unit controls said sound generator to generate an audible sound a predetermined time interval after said button has been depressed.

* * * * *